United States Patent [19]
Durette et al.

[11] Patent Number: 6,090,785
[45] Date of Patent: Jul. 18, 2000

[54] SUBSTITUTED N-CARBOXYALKYLPEPTIDYL DERIVATIVES AS ANTIDEGENERATIVE AGENTS

[75] Inventors: Philippe L. Durette, New Providence; Craig K. Esser, Belford; William K. Hagmann, Westfield; Ihor E. Kopka, Millburn, all of N.J.

[73] Assignee: Merck & Co., Inc., Rahway, N.J.

[21] Appl. No.: 07/961,307

[22] Filed: Oct. 15, 1992

[51] Int. Cl.$^7$ .................................................. A61K 38/05
[52] U.S. Cl. .............................. 514/19; 514/18; 530/331; 562/560; 562/575
[58] Field of Search .................. 514/19, 18; 435/212, 435/219; 424/94.67; 530/331; 562/560, 575

[56] References Cited

U.S. PATENT DOCUMENTS

| | | |
|---|---|---|
| 4,511,504 | 4/1985 | McCullugh et al. . |
| 4,568,666 | 2/1986 | McCullugh et al. . |
| 4,771,037 | 9/1988 | Roberts et al. . |
| 4,935,404 | 6/1990 | Hunter et al. . |
| 4,937,243 | 6/1990 | Markwell et al. . |
| 5,672,583 | 9/1997 | Chapman ................................... 514/19 |
| 5,932,551 | 8/1999 | Caldwell ................................... 514/19 |

FOREIGN PATENT DOCUMENTS

| | | |
|---|---|---|
| 0 079 521 | 5/1983 | European Pat. Off. . |
| 0 237 027 | 8/1987 | European Pat. Off. . |
| 0 274 234 | 7/1988 | European Pat. Off. . |
| 0 489 577 | 6/1992 | European Pat. Off. . |
| 0 489 579 | 6/1992 | European Pat. Off. . |

*Primary Examiner*—Michael P. Woodward
*Assistant Examiner*—David Lukton
*Attorney, Agent, or Firm*—James L. McGinnis; David L. Rose

[57] ABSTRACT

Novel N-carboxyalkylpeptidyl compounds represented by the formula

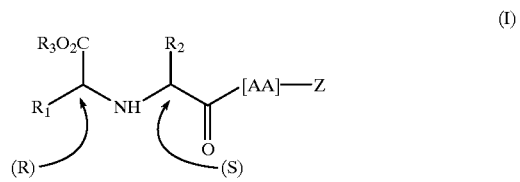

(I)

which are found to be useful inhibitors of matrix metalloendoproteinases which degrade major components of articular cartilage and basement membranes causing degenerative diseases such as arthritis, periodontal disease, corneal ulceration and the like, and certain cancers, are described.

21 Claims, No Drawings

SUBSTITUTED N-CARBOXYALKYLPEPTIDYL DERIVATIVES AS ANTIDEGENERATIVE AGENTS

BACKGROUND OF THE INVENTION

Novel N-carboxyalkylpeptidyl compounds of formula (I) are found to be useful inhibitors of matrix metalloendoproteinase-mediated diseases including osteoarthritis, rheumatoid arthritis, septic arthritis, tumor invasion in certain cancers, periodontal disease, corneal ulceration, proteinuria, dystrophobic epidermolysis bullosa, coronary thrombosis associated with atherosclerotic plaque rupture, and aneurysmal aortic disease. The matrix metalloendoproteinases are a family of zinc-containing proteinases including but not limited to stromelysin, collagenase, and gelatinase, that are capable of degrading the major components of articular cartilage and basement membranes. The inhibitors claimed herein may also be useful in preventing the pathological sequelae following a traumatic injury that could lead to a permanent disability. These compounds may also have utility as a means for birth control by preventing ovulation or implantation.

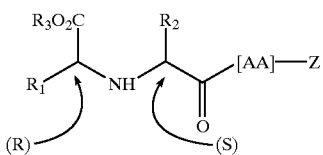

(I)

The disability observed in osteoarthritis (OA) and rheumatoid arthritis (RA) is largely due to the loss of articular cartilage. No therapeutic agent in the prior art is known to prevent the attrition of articular cartilage in these diseases.

"Disease modifying antirheumatic drugs" (DMARD), i.e., agents capable of preventing or slowing the ultimate loss of joint function in OA and RA are widely sought. Generic nonsteroidal antiinflammatory drugs (NSAIDs) may be combined with such agents to provide some relief from pain and swelling.

Stromelysin (aka. proteoglycanase, matrix metalloproteinase-3, MMP-3, procollagenase activator, "transin"), collagenase (aka. interstitial collagenase, matrix metalloproteinase-1(MMP-1)), and gelatinase (aka. type IV collagenase, matrix metalloproteinase-2, MMP-2, 72kDa-gelatinase or type V collagenase, matrix metalloproteinase-9, MMP-9, 95kDa-gelatinase) are metalloendoproteinases secreted by fibroblasts and chondrocytes, and are capable of degrading the major connective tissue components of articular cartilage or basement membranes. Elevated levels of both enzymes have been detected in joints of arthritic humans and animals: K. A. Hasty, R. A. Reife, A. H. Kang, J. M. Stuart, "The role of stromelysin in the cartilage destruction that accompanies inflammatory arthritis", Arthr. Rheum., 33, 388–97 (1990); S. M. Krane, E. P. Amento, M. B. Goldring, S. R. Goldring, and M. L. Stephenson, "Modulation of matrix synthesis and degradation in joint inflammation", in The Control of Tissue Damage", A. B. Glauert (ed.), Elsevier Sci. Publ., Amsterdam, 1988, Ch. 14, pp 179–95; A. Blanckaert, B. Mazieres, Y. Eeckhout, G. Vaes, "Direct extraction and assay of collagenase from human osteoarthrtic cartilage", Clin. Chim. Acta, 185 73–80 (1989). Each enzyme is secreted from these cells as an inactive proenzyme which is subsequently activated. There is evidence that stromelysin may be the in vivo activator for collagenase and gelatinase, implying a cascade for degradative enzyme activity: A. Ho, H. Nagase, "Evidence that human rheumatoid synovial matrix metalloproteinase 3 is an endogenous activator of procollagenase", Arch Biochem Biophys., 267, 211–16 (1988); G. Murphy, M. I. Crockett, P. E. Stephens, B. J. Smith, A. J. P. Docherty, "Stromelysin is an activator of procollagenase", Biochem. J., 248, 265–8 (1987); Y. Ogata, J. J. Enghild, H. Nagase, "Matrix metalloproteinase-3 (stromelysin) activates the precursor for human matrix metalloproteinase-9," J. Biol. Chem. 267,3581-84 (1992). Inhibiting stromelysin could limit the activation of collagenase and gelatinase as well as prevent the degradation of proteoglycan.

That stromelysin inhibition may be effective in preventing articular cartilage degradation has been demonstrated in vitro by measuring the effect of matrix metalloendoproteinase inhibitors on proteoglycan release from rabbit cartilage explants: C. B. Caputo, L. A. Sygowski, S. P. Patton, D. J. Wolanin, A. Shaw, R. A. Roberts, G. DiPasquale, J. Orthopaedic Res., 6, 103–8 (1988).

There is an extensive literature on the involvement of these metalloproteinases in arthritis, but there is very little to guide one in developing a specific inhibitor for each enzyme.

In preliminary studies of rabbit proteoglycanase with substrates and inhibitors, little was found to indicate the enzyme's requirements for hydrolysis or inhibition beyond a preference for hydrophobic residues at the $P_1$' position: A. Shaw, R. A. Roberts, D. J. Wolanin, "Small substrates and inhibitors of the metalloproteoglycanase of rabbit articular chondrocytes", Adv. Inflam. Res., 12, 67–79 (1988). More extensive studies with a series of substrates revealed that stromelysin will tolerate nearly every amino acid residue around the scissile bond: G. B. Fields, H. Brikedal-Hansen, H. E. Van Wart, unpublished results presented at the Matrix Metalloproteinase Conference, Sept. 1989, Sandestin Fla.

Human rheumatoid synovial collagenase has been shown to share ~50% homology with human stromelysin: S. E. Whitham, G. Murphy, P. Angel, H. J. Rahmsdorf, B. J. Smith, A. Lyons, T. J. R. Harris, J. J. Reynolds, P. Herrlich, A. J. P. Docherty, "Comparison of human stromelysin and collagenase by cloning and sequence analysis", Biochem. J., 240, 913–6 (1986). Many collagenase inhibitors have been designed around the cleavage site of the α-chain sequence of Type II collagen: W. H. Johnson, N. A. Roberts, N. Brokakoti, "Collagenase inhibitors: their design and potential therapeutic use", J. Enzyme Inhib., 2,1–22 (1987). One such inhibitor, N-[3-(benzyloxycarbonyl)amino-1-carboxy-n-propyl]-L-leucyl-O-methyl-L-tyrosine, N-methylamide, prepared at G. D. Searle, Inc., and shown to be a potent inhibitor of human rheumatoid synovial collagenase ($IC_{50}$= 0.8 $\mu$M), was also found to inhibit rabbit bone proteoglycanase ($IC_{50}$=0.5 $\mu$M): J. -M. Delaisse, Y. Eeckhout, C. Sear, A. Galloway, K. McCullagh, G. Vaes, "A new synthetic inhibitor of mammalian tissue collagenase inhibits bone resorption in culture", Biochem. Biophys. Res. Commun., 133, 483–90 (1985).

Gelatinase (MR ~72,000) has been isolated from rheumatoid fibroblasts: Y. Okada, T. Morodomi, J. J. Enghild, K. Suzuki, A. Yasui, I. Nakanishi, G. Salvesen, H. Nagase, "Matrix metalloproteinase 2 from human rheumatoid synovial fibroblasts", Eur. J., Biochem., 194, 721–30 (1990). The synthesis of the proenzyme is not coordinately regulated with the other two metalloproteinases and its activation may also be different. The role of gelatinase in the tissue destruction of articular cartilage appears different from the other two enzymes and, therefore, its inhibition may provide additional protection from degradation. A higher molecular weight gelatinase (MR 95,000; aka. type-V collagenase, matrix metalloproteinase-9, MMP-9) is also secreted by fibroblasts and monocytes and may be involved in cartilage degradation.

From the significant proportion of homology between human fibroblast collagenase, stromelysin, and gelatinase it is expected that a compound that inhibits one enzyme has a similar effect on all of them.

Compounds that inhibit collagenase, which possess structural portions akin to those of the instant invention include those encompassed by U.S. Pat. No. 4,511,504, U.S. Pat. No. 4,568,666, and EPO 126974A1, Compounds of related structure that are claimed to inhibit stromelysin (proteoglycanase) are encompassed by U.S. Pat. No. 4,771,037 and EPO 232027.

Stromelysin and collagenase inhibitors are believed to have utility in preventing articular cartilage damage associated with septic arthritis. Bacterial infections of the joints can elicit an inflammatory response that may then be perpetuated beyond what is needed for removal of the infective agent resulting in permanent damage to structural components. Bacterial agents have been used in animal models to elicit an arthritic response with the appearance of proteolytic activities. See J. P. Case, J. Sano, R. Lafyatis, E. F. Remmers, G. K. Kumkumian, R. L. Wilder, "Transin/stromelysin expression in the synovium of rats with experimental erosive arthritis", J. Clin Invest., 84, 1731–40 (1989); R. J. Williams, R. L. Smith, D. J. Schurman, "Septic Arthritis: Staphylococcal induction of chondrocyte proteolytic activity", Arthr. Rheum., 33, 533–41 (1990).

Inhibitors of stromelysin, collagenase, and gelatinase are believed to be useful to control tumor metastasis, optionally in combination with current chemotherapy and/or radiation. See L. M. Matrisian, G. T. Bowden, P. Krieg, G. Furstenberger, J. P. Briand, P. Leroy, R. Breathnach, "The mRNA coding for the secreted protease transin is expressed more abundantly in malignant than in benign tumors", Proc. Natl. Acad. Sci., USA, 83, 9413–7 (1986); S. M. Wilhelm, I. E. Collier, A. Kronberger, A. Z. Eisen, B. L. Marmer, G. A. Grant, E. A. Bauer, G. I. Goldberg, "Human skin fibroblast stromelysin: structure, glycosylation, substrate specificity, and differential expression in normal and tumorigenic cells", Ibid., 84, 6725–29 (1987); Z. Werb et al., Signal transduction through the fibronectin receptor induces collagenase and stromelysin gene expression, J. Cell Biol., 109, 872–889 (1989); L. A. Liotta, C. N. Rao, S. H. Barsky, "Tumor invasion and the extracellular matrix", Lab. Invest., 49, 636–649 (1983); R. Reich, B. Stratford, K. Klein, G. R. Martin, R. A. Mueller, G. C. Fuller, "Inhibitors of collagenase IV and cell adhesion reduce the invasive activity of malignant tumor cells", in Metastasis: Ciba Foundation Symposium; Wiley, Chichester, 1988, pp. 193–210.

Secreted proteinases such as stromelysin, collagenase, and gelatinase play an important role in processes involved in the movement of cells during metastatic tumor invasion. Indeed, there is also evidence that the matrix metalloproteinases are overexpressed in certain metastatic tumor cell lines. In this context, the enzyme functions to penetrate underlying basement membranes and allow the tumor cell to escape from the site of primary tumor formation and enter circulation. After adhering to blood vessel walls, the tumor cells use these same metalloendoproteinases to pierce underlying basement membranes and penetrate other tissues, thereby leading to tumor metastasis. Inhibition of this process would prevent metastasis and improve the efficacy of current treatments with chemotherapeutics and/or radiation.

These inhibitors should also be useful for controlling periodontal diseases, such as gingivitis. Both collagenase and stromelysin activities have been isolated from fibroblasts isolated from inflamed gingiva: V. J. Uitto, R. Applegren, P. J. Robinson, "Collagenase and neutral metalloproteinase activity in extracts of inflamed human gingiva", J. Periodontal Res., 16, 417–424(1981). Enzyme levels have been correlated to the severity of gum disease: C. M. Overall, O. W. Wiebkin, J. C. Thonard, "Demonstration of tissue collagenase activity in vivo and its relationship to inflammation severity in human gingiva", J. Periodontal Res., 22, 81–88 (1987).

Proteolytic processes have also been observed in the ulceration of the cornea following alkali burns: S. I. Brown, C. A. Weller, H. E. Wasserman, "Collagenolytic activity of alkali-burned corneas", Arch. Opthalmol., 81, 370–373 (1969). Mercapto-containing peptides do inhibit the collagenase isolated from alkali-burned rabbit cornea: F. R. Burns, M. S. Stack, R. D. Gray, C. A. Paterson, Invest. Opthalmol., 30, 1569–1575 (1989). Treatment of alkali-burned eyes or eyes exhibiting corneal ulceration as a result of infection with inhibitors of these metalloendoproteinases in combination with sodium citrate or sodium ascorbate and/or antimicrobials may be effective in preventing developing corneal degradation.

Stromelysin has been implicated in the degradation of structural components of the glomerular basement membrane (GBM) of the kidney, the major function of which is to restrict passage of plasma proteins into the urine; W. H. Baricos, G. Murphy, Y. Zhou, H. H. Nguyen, S. V. Shah, "Degradation of glomerular basement membrane by purified mammalian metalloproteinases", Biochem. J., 254, 609–612 (1988). Proteinuria, a result of glomerular disease, is excess protein in the urine caused by increased permeability of the GBM to plasma proteins. The underlying causes of this increased GBM permeability are unknown, but proteinases including stromelysin may play an important role in glomerular diseases. Inhibition of this enzyme may alleviate the proteinura associated with kidney malfunction.

Inhibition of stromelysin activity may prevent the rupturing of atherosclerotic plaques leading to coronary thrombosis. The tearing or rupture of atherosclerotic plaques is the most common event initiating coronary thrombosis. Destabilization and degradation of the connective tissue matrix surrounding these plaques by proteolytic enzymes or cytokines released by infiltrating inflammatory cells has been proposed as a cause of plaque fissuring. Such tearing of these plaques can cause an acute thrombolytic event as blood rapidly flows out of the blood vessel. High levels of stromelysin RNA message have been found to be localized to individual cells in atherosclerotic plaques removed from heart transplant patients at the time of surgery: A. M. Henney, P. R. Wakeley, M. J. Davies, K. Foster, R. Hembry, G. Murphy, S. Humphries, "Localization of stromelysin gene expression in atherosclerotic plaques by in situ hybridization", Proc. Nat'l. Acad. Sci. USA, 88, 8154–8158 (1991). Inhibition of stromelysin by these compounds may aid in preventing or delaying the degradation of the connective tissue matrix that stabilizes the atherosclerotic plaques, thereby preventing events leading to acute coronary thrombosis.

It is also believed that inhibitors of matrix metalloproteinases would have utility in treating degenerative aortic disease associated with thinning of the medial aortic wall. Aneurysms are often associated with atherosclerosis in this tissue. Increased levels of the degradative activities of the matrix metalloproteinases have been identified in patients with aortic aneurysms and aortic stenosis: N. Vine, J. T. Powell, "Metalloproteinases in degenerative aortic diseases", Clin. Sci., 81, 233–9 (1991). Inhibition of these enzymes may aid in preventing or delaying the degradation of aortic tissue, thus preventing events leading to acute and oftentimes fatal aortic aneurysms.

It is believed that specific inhibitors of stromelysin and collagenase should be useful as birth control agents. There is evidence that expression of metalloendoproteinases, including stromelysin and collagenase, is observed in unfertilized eggs and zygotes and at further cleavage stages and increased at the blastocyst stage of fetal development and with endoderm differentiation: C. A. Brenner, R. R. Adler, D. A. Rappolee, R. A. Pedersen, Z. Werb, "Genes for extracellular matrix-degrading metalloproteinases and their inhibitor, TIMP, are expressed during early mammalian development", Genes & Develop., 3, 848–59 (1989). By analogy to tumor invasion, a blastocyst may express metalloproteinases in order to penetrate the extracellular matrix of the uterine wall during implantation. Inhibition of stromelysin and collagenase during these early developmental processes should presumably prevent normal embryonic development and/or implantation in the uterus. Such intervention would constitute a novel method of birth control. In addition there is evidence that collagenase is important in ovulation processes. In this example, a covering of collagen over the apical region of the follicle must be penetrated in order for the ovum to escape. Collagenase has been detected during this process and an inhibitor has been shown to be effective in preventing ovulation: J. F. Woessner, N. Morioka, C. Zhu, T. Mukaida, T. Butler, W. J. LeMaire "Connective tissue breakdown in ovulation", Steroids, 54, 491–499 (1989). There may also be a role for stromelysin activity during ovulation: C. K. L. Too, G. D. Bryant-Greenwood, F. C. Greenwood, "Relaxin increases the release of plasminogen activator, collagenase, and proteo-glycanase from rat granulosa cells in vitro", Endocrin., 115, 1043–1050 (1984).

Collagenolytic and stromelysin activity have also been observed in dystrophobic epidermolysis bullosa: A. Kronberger, K. J. Valle, A. Z. Eisen, E. A. Bauer, J. Invest. Dermatol., 79 208–211 (1982); D. Sawamura, T. Sugawara, I. Hashimoto, L. Bruckmer-Tuderman, D. Fujimoto, Y. Okada, N. Utsumi, H. Shikata, Biochem. Biophys. Res. Commun., 174, 1003–8 (1991). Inhibition of metalloendoproteinases should limit the rapid destruction of connective components of the skin.

In addition to extracellular matrix comprising structural components, stromelysin can degrade other in vivo substrates including the inhibitors $\alpha_1$-proteinase inhibitor and may therefore influence the activities of other proteinases such as elastase: P. G. Winyard, Z. Zhang, K. Chidwick, D. R. Blake, R. W. Carrell, G. Murphy, "Proteolytic inactivation of human $\alpha_1$-antitrypsin by human stromelysin", FEBS Letts., 279, 1, 91–94 (1991). Inhibition of the matrix metalloendoproteinases may potentiate the antiproteinase activity of these endogenous inhibitors.

SUMMARY OF THE INVENTION

The invention encompasses novel N-carboxyalkylpeptidyl compounds which are useful inhibitors of matrix metalloendoproteinase-mediated diseases including degenerative diseases (such as defined above) and certain cancers.

DETAILED DESCRIPTION OF THE INVENTION

The invention encompasses compounds of formula (I)

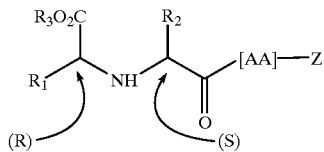

(I)

or a pharmaceutically acceptable salt thereof wherein:

$R_1$ is substituted $C_{1-6}$alkyl, wherein the substituent is elected from the group consisting of:

(a) hydrogen, (b) carboxy, (c)

(d) $C_{6-10}$aryl wherein the aryl group is elected from the group consisting of
(1) phenyl,
(2) naphthyl,
(3) pyridyl,
(4) furyl,
(5) pyrryl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl,
(23) isoxazolyl,
(24) thiazolyl,
(25) oxazolyl,
(26) benzthiazolyl, and
(27) benzoxazolyl, and mono and di-substituted $C_{6-10}$aryl wherein aryl is as defined above in items (1) to (27) wherein the substituents are independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, and $C_{1-6}$alkylcarbonyl;

(e)

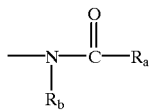

wherein $R_a$ and $R_b$ are each independently hydrogen; $C_{6-10}$aryl and mono and di-substituted $C_{6-10}$aryl as defined above (d); or substituted $C_{1-6}$alkyl wherein the substituent is selected from hydroxy, halo, and phenyl; or wherein Ra and Rb are joined such that together with the nitrogen and carbon atoms to which they are attached, there is formed a lactam or benzolactam ring wherein the lactam portion thereof is a ring of up to 8 atoms, said lactam or benzolactam having a single hetero atom;

(f)

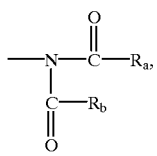

wherein $R_a$ and $R_b$ are each independently hydrogen; $C_{6-10}$aryl and mono and di-substituted $C_{6-10}$aryl as defined above (d); or substituted $C_{1-6}$alkyl wherein the substituent is selected from hydroxy, halo, and phenyl, or wherein $R_a$ and $R_b$ are joined such that together with the nitrogen and carbon atoms to which they are attached, there is formed a lactim or benzolactim ring wherein the lactim portion thereof is a ring of up to 8 atoms, said lactim or benzolactim have a single hetero atom;

(g) amino and substituted amino wherein the substituent is selected from $C_{1-6}$alkyl and $C_{6-10}$aryl wherein aryl is as defined in (d);

$R_2$ is substituted $C_{7-12}$alkyl wherein the substituent is hydrogen, amino, $C_{1-3}$alkylamino, $C_{1-3}$dialkylamino, or hydroxyl;

$R_3$ is
(a) H,
(b) $C_{1-10}$alkyl,
(c) $C_{6-10}$aryl or $C_{6-10}$aryl $C_{1-3}$alkyl, wherein the aryl group is selected from the group consisting of
  (1) phenyl, and
  (2) substituted phenyl, wherein the substituent is carboxy, carboxy$C_{1-3}$alkyl, aminocarbonyl, $C_{1-6}$alkylaminocarbonyl;

AA is an amino acid radical represented by (II)

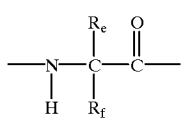

wherein $R_e$ and $R_f$ are individually selected from:
(a) hydrogen,
(b) $C_{1-6}$alkyl,
(c) mercapto $C_{1-6}$alkyl,
(d) hydroxy $C_{1-6}$alkyl,
(e) carboxy $C_{1-6}$alkyl,
(f) amino substituted $C_{2-6}$alkyl
(g) aminocarbonyl $C_{1-6}$alkyl,
(h) mono- or di-$C_{1-6}$alkyl amino $C_{2-6}$alkyl,
(i) guanidino $C_{2-6}$alkyl,
(j) substituted phenyl $C_{1-6}$alkyl, wherein the substituent is hydrogen, hydroxy, carboxy, $C_{1-4}$ alkyl, or $C_{1-4}$alkyloxy,
(k) substituted indolyl $C_{1-6}$alkyl, wherein the substituent is hydrogen, hydroxy, carboxy, $C_{1-4}$ alkyl, or $C_{1-4}$alkyloxy,
(l) substituted imidazolyl $C_{2-6}$alkyl wherein the substituent is hydrogen, hydroxy, carboxy, $C_{1-4}$ alkyl, or $C_{1-4}$alkyloxy,
(m) substituted pyridyl $C_{1-6}$alkyl wherein the substituent is hydrogen, hydroxy, carboxy, $C_{1-4}$ alkyl, or $C_{1-4}$alkyloxy,
(n) substituted pyridylamino $C_{1-6}$alkyl wherein the substituent is hydrogen, hydroxy, carboxy, $C_{1-4}$ alkyl, or $C_{1-4}$alkyloxy, Z is

wherein $R_5$ and $R_6$ are each individually selected from the group consisting of:
(a) H,
(b) $C_{1-10}$alkyl,
(c) $C_{6-10}$aryl or $C_{6-10}$aryl$C_{1-6}$alkyl, wherein the aryl group is selected from the group consisting of
  (1) phenyl,
  (2) naphthyl,
  (3) pyridyl,
  (4) pyrryl,
  (5) furyl,
  (6) thienyl,
  (7) isothiazolyl,
  (8) imidazolyl,
  (9) benzimidazolyl,
  (10) tetrazolyl,
  (11) pyrazinyl,
  (12) pyrimidyl,
  (13) quinolyl,
  (14) isoquinolyl,
  (15) benzofuryl,
  (16) isobenzofuryl,
  (17) benzothienyl,
  (18) pyrazolyl,
  (19) indolyl,
  (20) isoindolyl,
  (21) purinyl,
  (22) carbazolyl,
  (23) isoxazolyl,
  (24) benzthiazolyl,
  (25) benzoxazolyl
  (26) thiazolyl, and
  (27) oxazolyl.

The amino acids of above amino acid radical of formula II are intended to be inclusive of acids such as glycine, alanine, valine, leucine, isoleucine, serine, threonine, aspartic acid, asparagine, glutamic acid, glutamine, lysine, hydroxylysine, arginine, homohistidine, phenylalanine, tyrosine, tryptophan, cysteine, methionine, ornithine, homoserine, and citrulline.

One preferred genus of this embodiment is that embracing compounds wherein:

$R_1$ is substituted $C_{1-6}$alkyl, wherein the substituent is selected from the group consisting of:
(a) hydrogen,
(b) carboxy,
(c)

(d) $C_{6-10}$aryl or $C_{6-10}$aryl $C_{6-10}$ alkyl wherein the aryl group is selected from the group consisting of
(1) phenyl,
(2) naphthyl,
(3) thienyl,
(4) imidazolyl,
(5) benzimidazolyl,
(6) pyrimidyl,
(7) benzofuryl,
(8) benzothienyl,
(9) indolyl, and mono and di-substituted $C_{6-10}$aryl as defined above in items (1) to (9) wherein the substitutents are independently selected from $C_{1-6}$alkyl, $C_{1-6}$alkyloxy, halo, hydroxy, amino, $C_{1-6}$alkylamino, and $C_{1-6}$alkylcarbonyl;
(e)

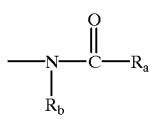

wherein $R_a$ and $R_b$ are each independently hydrogen, $C_{6-10}$ aryl wherein the aryl group is selected from the group consisting of
(1) phenyl,
(2) naphthyl,
(3) thienyl,
(4) imidazolyl,
(5) benzimidazolyl,
(6) pyrimidyl,
(7) benzofuryl,
(8) benzothienyl,
(9) indolyl, and mono and di-substituted $C_{6-10}$ aryl as defined above; or substituted $C_{1-6}$alkyl wherein the substitutent is selected from hydroxy, halo, and benzyl, or wherein Ra and Rb are joined together to form a lactam or benzolactam ring as defined above.

One class of this genus is that of compounds in which:
$R_2$ is
substituted $C_{8-10}$alkyl wherein the substituent is hydrogen or amino;

A sub-class of this class is that of compounds in which:
$R_3$ is
(a) H,
(b) $C_{1-10}$alkyl,
(c) phenyl, substituted phenyl, wherein the substituent is carboxy, carboxy $C_{1-3}$alkyl, amino carbonyl.

Within this sub-class are the compounds in which:
AA is an amino acid including glycine, alanine, valine, leucine, isoleucine, serine, threonine, aspartic acid, asparagine, glutamic acid, glutamine, lysine, hydroxylysine, homohistidine, arginine, phenylalanine, tyrosine, tryptophan, cysteine, methionine, ornithine, homoserine, or citrulline.

Alternatively, within this sub-class the amino acids AA can be defined as follows:
AA is

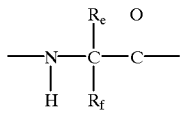

wherein $R_e$ and $R_f$ are individually selected from:
(a) hydrogen,
(b) $C_{1-4}$alkyl,
(c) mercapto $C_{1-3}$alkyl,
(d) hydroxy $C_{1-4}$alkyl,
(e) carboxy $C_{1-4}$alkyl,
(f) amino $C_{2-4}$alkyl,
(g) aminocarbonyl $C_{1-4}$alkyl,
(h) mono- or di-$C_{2-6}$alkyl amino $C_{2-4}$alkyl,
(i) guanidino $C_{2-4}$alkyl,
(j) substituted phenyl $C_{1-4}$alkyl, wherein the substituent is hydrogen, hydroxy, carboxy, or $C_{1-3}$ alkyl,
(k) substituted indolyl $C_{1-4}$alkyl, wherein the substituent is hydrogen, hydroxy, carboxy, or $C_{1-3}$ alkyl,
(l) substituted imidazolyl $C_{2-6}$alkyl wherein the substituent is hydrogen, hydroxy, carboxy, or $C_{1-4}$ alkyl.

A further preferred group of compounds may be identified as that wherein Z is

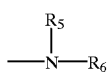

wherein $R_5$ and $R_6$ are each individually selected from the group consisting of
(a) H,
(b) $C_{1-10}$alkyl, or
(c) $C_{6-10}$aryl, or $C_{6-10}$aryl$C_{1-6}$alkyl wherein the aryl group is selected from the group consisting of
(1) phenyl,
(2) naphthyl,
(3) thienyl,
(4) imidazolyl,
(5) benzimidazolyl,
(6) pyrimidyl,
(7) benzofuryl,
(8) benzothienyl,
(9) indolyl, and
(10) pyridyl.

A smaller especially preferred group within this group are the compounds wherein:
$R_3$ is
(a) H, or
(b) $C_{1-10}$alkyl; and
$R_1$ is $C_{6-10}$aryl $C_{1-6}$alkyl.

Exemplifying the invention and most preferred are the following compounds:
(a) N-[1(R)-carboxyethyl]-α-(S)-(9-aminononyl)]glycine-(L)-Leucine, N-phenylamide;
(b) N-[1(R)-carboxyethyl]-α-(S)-(n-octyl)]glycine-(L)-Leucine, N-phenylamide;

(c) N-[1(R)-carboxyethyl]-α-(S)-(n-octyl)]glycine-(L)-Arginine, N-phenylamide;

(d) N-[1(R)-carboxyethyl]-α-(S)-(9-amino-n-nonyl)]-glycine-(L)-Arginine, N-phenylamide;

(e) N-[1(R)-carboxyethyl]-α-(S)-(n-decyl)]glycine-(L)-Leucine, N-phenylamide;

This invention also concerns pharmaceutical composition and methods of treatment of stromelysin-mediated or implicated disorders or diseases (as described above) in a patient (which shall be defined to include man and/or mammalian animals raised in the dairy, meat, or fur industries or as pets) in need of such treatment comprising administration of the stromelysin inhibitors of formula I as the active constituents.

Similarly, this invention also concerns pharmaceutical compositions and methods of treatment of collagenase mediated or implicated disorders or diseases (as described above) in a patient in need of such treatment comprising administration of the collagenase inhibitors of formula (I) as the active constituents.

Similarly, this invention also concerns pharmaceutical compositions and methods of treatment of gelatinase-mediated or implicated disorders or diseases (as described above) in a patient in need of such treatment comprising administration of the gelatinase inhibitors of formula (I) as the active constituents.

Moreover the invention also encompasses compositions, treatment, and method for co-administration of a compound of formula I with a PMN elastase inhibitor such as those described in EP 0 337 549 which published on Oct. 18, 1989, Compounds of the instant invention are conveniently prepared using the procedures described generally below in the flow diagram, Scheme I, and more explicitly described in the Example section thereafter.

SCHEME 1 a: Benzyl chloroformate, aq. NAHCO$_3$
b: Trimethylacetyl chloride, TEA
   (S)-(-)-4-Benzyl-2-oxazolidinone, n-BuLi
c: KN(SiMe$_3$)$_2$, Trisyl-N$_3$, AcOH
d: LiOH, H$_2$O$_2$
e: [AA]-Z, HOBt, EDC

*n = 6-11 in above formulas
**R = protected or substituted amino group; or H
Bn = benzyl f: SnCl$_2$, MeOH
g: (S)-Benzyl lactate, Tf$_2$O, 2, 6-Lutidine, Et($^i$Pr)$_2$N
h: H$_2$, Pd(OH)$_2$ An appropriate alkyl or protected aminoalkyl carboxylic acid (2) is converted to α-azido acid (5) by methodology described by Evans and Britton, J. Am. Chem. Soc. 112, 4011 (1990). Specifically, in Step (b), the azido acid (2) is treated with trimethylacetyl chloride and triethylamine (TEA) and reacted with the lithium salt of (S)-(−)-4-benzyl-2-oxazolidinone to form compound of formula (3). Azide transfer is effected (Step c) by generating potassium anion of (3) and reacting with 2,4,6-triisopropylphenylsulfonyl azide (trisyl azide) in acetic acid (AcOH) to form compound (4).

In Step (d), hydrogen peroxide hydrolysis under basic conditions of the acyloxazolidinone (4) produces the free acid (5). Reaction of acid (5) with a derivatized amino acid [AA]-Z (Step e) yields an azidopeptide (6). Reduction of the azide group with stannous chloride (Step f) in methanol (MeOH) produces the free amine (7). Reaction of (7) with the triflate of benzyl (S)-lactate in the prescence of 2,6-lutidine and diisopropylethylamine (Et($^i$Pr)$_2$N) (Step g) yields the N-carboxyalkylpeptide benzyl ester (8). Hydrogenolysis of the benzyl ester (8) (Step h) yields the free acid (9).

Compounds of the present invention have inhibitory activities with respect to metalloendoproteinases such as stromelysin, collagenase and gelatinase. The activities of the compounds against these enzymes may be seen in representative assays.

The capacity to inhibit the hydrolysis by stromelysin may be demonstrated in an assay in which the extent of enzymatic cleavage of a substrate Arg-Pro-Lys-Pro-Leu-Ala-Phe-TrpNH$_2$ (SEQ ID NO:1) at the Ala-Phe is determined fluorometrically (excitation gamma=280 nm; emission gamma=345 nm) with varying concentrations of inhibitor. Briefly the assay may be carried out by incubating for four hours the inhibitor in dimethyl sulfoxide (DMSO) and 25 µl of 0.3726 µg/ml stromelysin, then adding 60 µl of 11.24 µM substrate and incubating the resulting mixture for 18 hours. The final concentrations of the substrate is 5 µM and of the enzyme 1.5 nM. At this time 50 µl of 0.3 M H$_3$PO$_4$ is added and a portion of the mixture injected onto an HPLC column and the remaining substrate determined by fluorometric detection. The area of the substrate is quantitated and is plotted as a function of the inhibitor concentration. The K$_i$ is calculated using the following equation:

$$\frac{area_{inhibited}}{area_{control}} = \frac{1}{1+[I]/Ki} \text{ and where } [S] \ll Km$$

where $_{area}$inhibited and $^{area}$control are integrated HPLC areas for substrate for inhibited and uninhibited reactions, respectively; [I] is the inhibitor concentration; [S] is the substrate concentration.

The results for stromelysin may be seen in Table 1.

The capacity of representative compounds of formula I to inhibit collagenase and gelatinase lysis may be determined using the method of M. S. Stack et al, Biol. Chem 264, 4277 (1989). In such assay, a fluorogenic substrate Dnp-Pro-Leu-Gly-Leu-Trp-Ala-D-Arg.(SEQ ID NO:2) where the "Dnp" designation indicates a "dinitrophenyl" group and this group is indicated by "Xaa" in the Sequence Listing. is used. The tryptophan fluorescence is efficiently quenched by the dinitrophenyl group but when it is hydrolyzed by collagenase or gelatinase, there is increased fluorescence with cleavage occurring at the Gly-Leu bond.

Assays were performed in 0.05M Tris, 5 mM CaCl$_2$, 0.2M NaCl up to 20% Me$_2$SO, pH 7.7 at either 250 or 37° C. using peptide concentrations of 2.5 to 40 µM.

After addition of enzyme to initiate the reaction, the initial rate of substrate hydrolysis is determined by monitoring the increase in fluorescence emission at 346 nm. using an excitation wavelength of 280 nm. To determine the inhibitory activity the hydrolysis is measured fluorimetrically in the presence of increasing concentrations of the inhibitor and the K$_i$ is determined.

This invention also relates to a method of treatment for patients (including man and/or mammalian animals raised in the dairy, meat, or fur industries or as pets) suffering from disorders or diseases which can be attributed to stromelysin as previously described, and more specifically, a method of treatment involving the administration of the matrix metalloendoproteinase inhibitors of formula (I) as the active constituents.

Accordingly, the compounds of formula (I) can be used among other things in the treatment of osteoarthritis and rheumatoid arthritis, and in diseases and indications resulting from the over-expression of these matrix metalloendoproteinases such as found in certain metastatic tumor cell lines.

For the treatment of rheumatoid arthritis, osteoarthritis, and in diseases and indications resulting from the over-expression of matrix metalloendoproteinases such as found in certain metastatic tumor cell lines or other diseases mediated by the matrix metalloendoproteinases, the compounds of formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compounds of the invention are effective in the treatment of human beings.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and

TABLE 1

| Compound | R$_1$ | R$_2$ | R$_3$ | [AA] | Z | Inhibition K$_I$ (µM) | | |
| --- | --- | --- | --- | --- | --- | --- | --- | --- |
| | | | | | | SLN* | CGase* | Gel* |
| 9a | CH$_3$ | n-C$_9$H$_{18}$NH$_2$ | H | (L)-Leu | NHPh* | 0.24 | >10 | 0.50 |
| 9b | CH$_3$ | n-C$_8$H$_{17}$ | H | (L)-Leu | NHPh | 0.57 | >10 | 0.34 |
| 9c | CH$_3$ | n-C$_8$H$_{17}$ | H | (L)-Arg | NHPh | 1.6 | | 0.12 |
| 9d | CH$_3$ | n-C$_9$H$_{18}$NH$_2$ | H | (L)-Arg | NHPh | 0.37 | | 0.11 |
| 9e | CH$_3$ | n-C$_{10}$H$_{21}$ | H | (L)-Leu | NHPh | 0.85 | | 0.56 |

*Ph = phenyl
SLN = stromelysin
CGase = collagenase
Gel = gelatinase preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid or butylated hydroxyanisole (BHA).

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula (I) are employed. (For purposes of this application, topical application shall include mouth washes and gargles.)

Dosage levels of the order of from about 0.05 mg to about 140 mg per kilogram of body weight per day are useful in the treatment of the above-indicated conditions (about 2.5 mg to about 7 gms. per patient per day). For example, inflammation may be effectively treated by the administration of from about 0.01 to 50 mg of the compound per kilogram of body weight per day (about 0.5 mg to about 3.5 gms per patient per day).

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Examples are intended to illustrate the preparation of compounds of Formula I, and as such are not intended to limit the invention as set forth in the claims appended, thereto.

EXAMPLE 1
N-[1(R)-carboxyethyl]-α-(S)-(9-aminononyl)]glycine-(S)-Leucine, N-phenylamide (9a)
N-CBz-11-amino-n-undecanoic acid (2a)

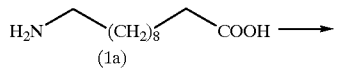
(1a)

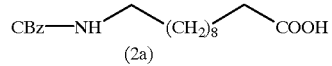
(2a)

4.0 g (19.9 mmol) of 11-amino-n-undecanoic acid was dissolved in 100 ml of 1 N NaHCO$_3$. THF was slowly added until the starting material began to precipitate out of solution. The mixture was cooled to 0° C., then 4.3 ml (29.8 mmol) of benzyl chloroformate added. The cooling bath was removed and the reaction mixture stirred for 16 hours then diluted with EtOAc. A white precipitate formed in the organic layer. The organic layer was washed with a saturated solution of sodium chloride. The organic layer was concentrated then redissolved in MeOH. The remaining solids were filtered off and the filtrate cooled to −78° C. to precipitate out the product. The product was recovered by filtration and washed with cooled MeOH, and air dried. 5.76 g of white solid was recovered. Yield =86% 3-(11-benzyloxycarbonylamino-n-undecanoyl)-4(S)-(phenylmethyl)--2-oxazolidinone (3a)

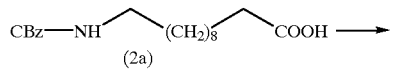
(2a)

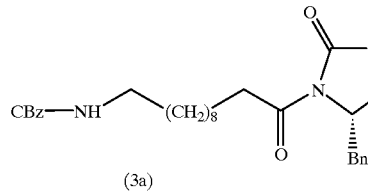
(3a)

To a solution of 5.75 g (17.1 mol) of 2 in 150 ml of freshly distilled THF at −78° was added 3.11 ml (22.3 mmol) of triethylamine, followed by 2.32 ml (18.9 mmol) of trimethylacetylchloride. The resulting slurry was stirred at −78° for 15 min., then at 0° for 2 hours, then recooled to −78°. In a separate flask, to a cooled solution (−78°) of 5.47 g (30.9 mmol) of (S)-(−)-4-benzyl-2-oxazolidinone in 100 ml of THF was added 19.8 ml (31.7 mmol) of n-butyllithium (1.6 M in hexane), and the resulting mixture stirred at −78° for 1 hour, then added to the slurry of the mixed anhydride at −78° via canula. The cooling bath was removed and the mixture stirred for 2 hours. Thereafter it was quenched with 1N KHCO$_3$ and stir for 30 min. The THF was evaporated in vacuo, then the aqueous layer extracted with CHCl$_3$. The organic layer was washed with saturated NaCl, dried over MgSO$_4$, filtered and concentrated to obtain an oil. The resulting oil was purified by medium pressure chromatography on silica gel with 25% EtOAc in hexane as eluent and 5.43 g of white solid recovered. Yield=64%.
3-(2(S)-azido-11-benzyloxycarbonylamino-n-undecanoyl)-4(S)-(phenylmethyl)-2-oxazolidinone (4a)

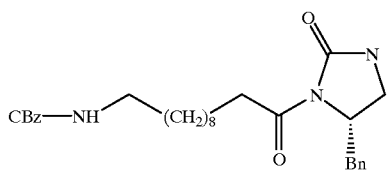
(3a)

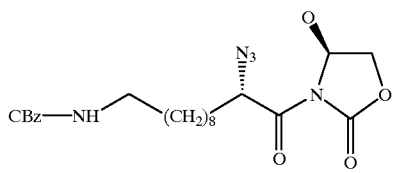
(4a)

63.1 mL (25.2 mmol) of potassium bis(trimethylsilyl) amide (0.4 M in toluene) was dissolved in 63.1 ml of dry THF under nitrogen in a flame dried flask. To it was added a precooled solution (−78°) of 5.43 g (10.98 mmol) of 3 in 36.6 ml of dry THF. The mixture was stirred for 1 hour, then added to a precooled solution (−78°) of 4.08 g (13.2 mmol) of 2,4,6-triisopropylbenzenesulfonyl azide in 44 ml of dry THF and stirred for 2 min. To it then was added 2.9 ml (50.5 mmol) of glacial acetic acid in one portion. The cooling bath was removed and the mixture stirred for 16 hours. At the end of this period, the mixture was diluted with sat. NaCl and CHCl$_3$, the aqueous layer extracted with CHCl$_3$ and the organic layer dried over MgSO$_4$. The dried solution was concentrated and purified by medium pressure chromatography on silica gel with 1% EtOAc in CH$_2$Cl$_2$ as eluent to recover 2.25 g of yellow oil. Yield =38%.
2(S)-Azido-11-benzyloxycarbonylamino-n-undecanoic acid (5a)

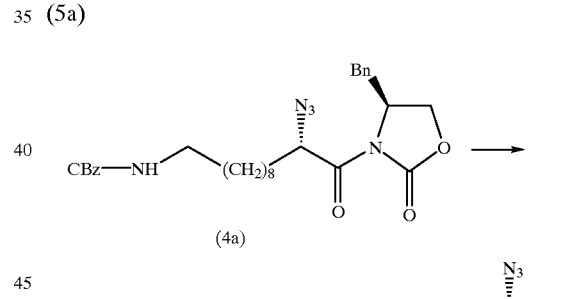
(4a)

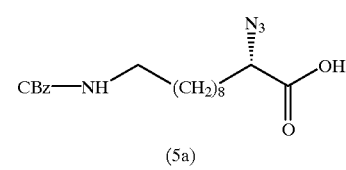
(5a)

2.25 g (4.2 mmol) of 4a prepared as above described was dissolved in a solution of 100 ml of 3:1 THF/H$_2$O and the mixture cooled to 00 and to it was added 1.91 ml (16.8 mmol) of 30% hydrogen peroxide, followed by 353 mg (8.4 mmol) of LiOH hydrate. The resulting mixture was stirred for 1 hour. The ice bath was removed and a solution of 2.3 g (18.5 mmol) of sodium bisulfate in 20 ml of water and 50 ml of 0.5 N NaHCO$_3$ was added and stirred for 2 hours. The THF was evaporated in vacuo and the residue diluted with water. The aqueous layer was extracted with CH$_2$Cl$_2$ to extract the chiral auxiliary. An emulsion formed that would not break up, so CH$_2$Cl$_2$ was evaporated in vacuo and the resulting aqueous layer extracted with EtOAc. The EtOAc solution was concentrated in vacuo to obtain an oil which was redissolved in water and acidified to pH=2 with 2 N HCl. The aqueous layer was extracted with EtOAc, dried over MgSO₄, filtered concentrated, and purified by medium pressure chromatography on silica gel with 5% MeOH in CHCl₃ as eluent. 2.1 g of a 1:1 mixture of the desired product and the chiral auxiliary were recovered. It was used as is without further purification.

N-(2(S)-Azido-11-benzyloxycarbonylamino-n-undecanoyl)-(L)-leucine, N'-phenylamide (6a)

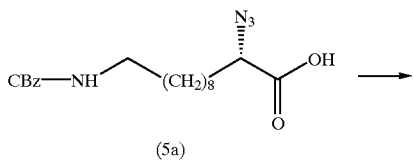

(5a)

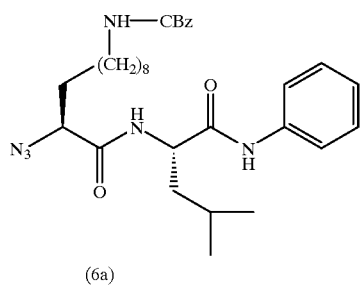

(6a)

300 mg (0.8 mmol) of (5a) was dissolved in 5 ml of dry THF and to it was added 129 mg (0.96 mmol) of 1-hydroxybenzotriazole hydrate and 197 mg (0.96 mmol) of (L)-leucinanilide. The mixture was stirred for 30 min. at 25°, then to it was added 306 mg (1.6 mmol) of 1-(3-dimethylaminopropyl)-3-ethylcarbodiimide hydrochloride and stired at 25° for 16 hours. The mixture then was diluted with sat. NaHCO₃ and EtOAc and the aqueous layer extracted with EtOAc. The organic layers were washed with sat. NaHCO₃ and sat. NaCl and dried over MgSO₄, then filtered and concentrated. The residue was purified by medium pressure chromatography on silica gel with 30% EtOAc in hexane as eluent and 320 mg of yellow oil recovered. Yield =71%.

α-(S)-(9-benzyloxycarbonylamino-n-nonyl)glycine-(L)-leucine, N-phenylamide (7a)

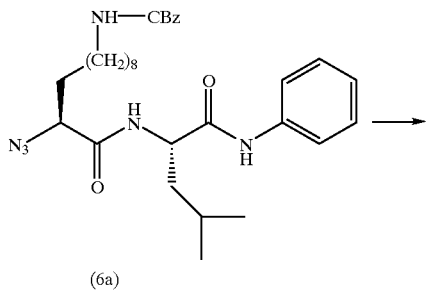

(6a)

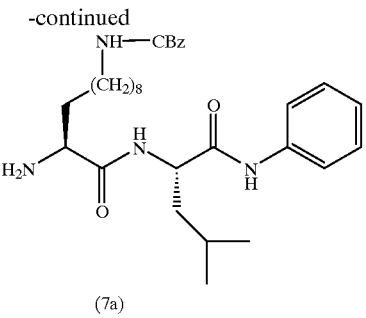

(7a)

161 mg (0.85 mmol) of tin(II) chloride was vigorously stirred in 2 ml of MeOH at 0°. 320 mg (0.57 mmol) of (6a) was dissolved in 2 ml of MeOH and this solution added to the tin solution dropwise at 0° stirred then at ambient temperature for 3 hours. MeOH was evaporated in vacuo and the resulting oil diluted with 2 N NaOH and EtOAc. The aqueous layer was extracted with EtOAc using sat. NaCl to make the aqueous layer more ionic and the combined EtOAc layers dried over MgSO₄, the dried solution filtered and concentrated to recover 300 mg of yellow oil. Yield =98%.

Benzyl-N-[1(R)-carboxyethyl]-α-(S)-(9-benzyloxycarbonyl-n-nonyl)]glycine-(L)-Leucine. N-phenylamide (8a)

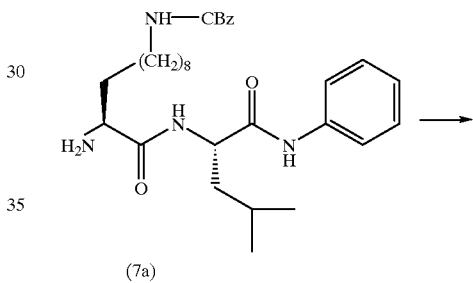

(7a)

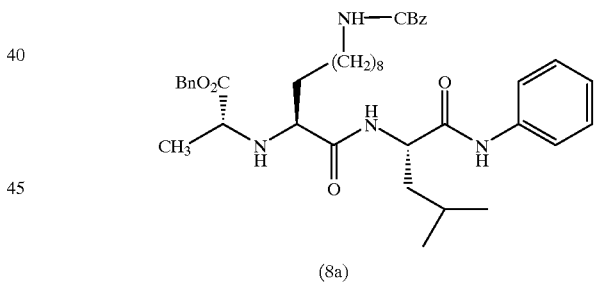

(8a)

120 mg (0.67 mmol) of benzyl (S)-lactate was dissolved in 2 ml of CH₂Cl₂. The solution was cooled to 00, then 0.124 ml (0.74 mmol) of trifluoromethanesulfonic anhydride added dropwise over 5 min. under nitrogen atmosphere. The resulting mixture was stirred for 5 min., then 0.99 ml (0.85 mmol) of 2,6-lutidine added in one portion and stirred for 10 min. Then 0.141 ml (0.81 mmol) of diisopropylethylamine was added, followed immediately by a solution of 300 mg (0.56 mmol) of (7a) in 2 ml of CH₂Cl₂ in a dropwise manner. The mixture was then stirred for 16 hours at room temperature. Thereafter it was diluted with sat. NaHCO₃ and CH₂Cl₂, the organic layer then was washed with sat. NaHCO₃ and sat. NaCl, and dried over MgSO₄. The dried solution was concentrated and purified by medium pressure chromatography on silica gel with 12% ethyl acetate in CH₂Cl₂ as eluent to recover 219 mg of yellow oil. Yield =56%.

N-[1(R)-carboxyethyl]-α-(S)-(9-amino-n-nonyl)]glycine-(L)-Leucine, N-phenylamide (9a)

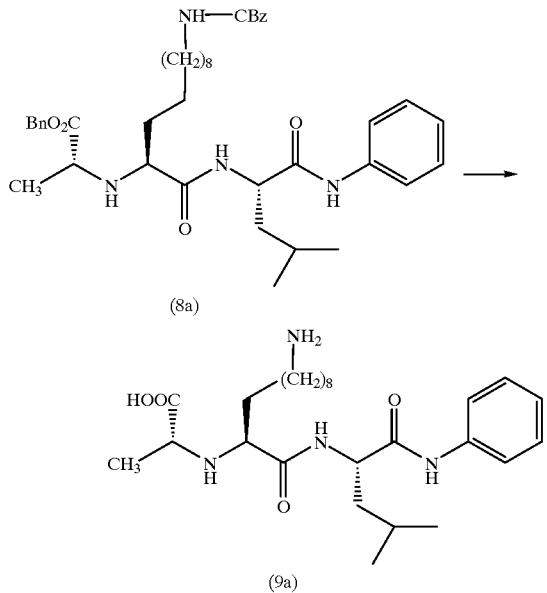

(8a)

(9a)

219 mg (0.31 mmol) of (8a) was dissolved in 2 ml of MeOH and 20 mg of Pearlman's catalyst and hydrogen gas added by balloon. The mixture was stirred at 25° for 3 hours. Filtered and the solvent evaporated in vacuo. 144 mg of (9a) was recovered as a white solid. Yield=98%. MS: m/z 477.5 (M+); $^1$H NMR: (CD$_3$OD, δ, 400 MHz) 7.56 (d, J=7 Hz, 2H), 7.30 (dd, J=8 Hz, 2H), 7.09 (dd, J=8 Hz, 1H), 4.61 (dd, J=6 Hz, 1H), 3.88 (t, J=7 Hz, 1H), 3.54 (q, J=7 Hz, 3H), 2.86 (t, J=8 Hz, 2H), 1.85–1.55 (m, 4H), 1.46 (d, J=7 Hz, 3H), 1.43–1.19 (m, 15H), 0.99 (dd, J=7 Hz, 6H).

The following compounds were prepare by the methods described in Example 1:

EXAMPLE 2
N-[1(R)-carboxyethyl]-α-(S)-(n-octyl)]glycine-(L)-Leucine, N-phenylamide (9b)

MS: m/z 448.8 (M$^{30}$); $^1$H NMR: (CD$_3$OD, δ, 400 MHz) 7.55 (d, J=7 Hz, 2H), 7.29 (dd, J=8 Hz, 2H), 7.09 (dd, J=8 Hz, 1H), 4.64 (dd, J=6 Hz, 1H), 3.92 (t, J=7 Hz, 1H), 3.62 (q, J=7 Hz, 3H), 1.86–1.64 (m, 4 H), 1.49 (d, J=7 Hz, 3H), 1.32 (m, 1H), 1.22 (m, 12 H), 1.00 (dd, J=7 Hz, 6H), 0.85 (t, J=7 Hz, 3H). Elem. anal. Calcd. for C$_{25}$H$_{41}$N$_3$O$_4$ +0.55 H$_2$O: C, 65.63; H, 9.27; N, 9.18. Found: C, 65.58; H, 9.38; N, 9.22.

EXAMPLE 3
N-[1(R)-carboxyethyl]-α-(S)-(n-octyl)]glycine-(L)-Arginine, N-phenylamide (9c)

MS: m/z 491 (M+); $^1$H NMR: (CD$_3$OD, δ, 400 MHz) 7.56 (d, J=7 Hz, 2H), 7.27 (dd, J=8 Hz, 2H), 7.07 (dd, J=8 Hz, 1H), 4.55 (dd, J=5 Hz, 1H), 3.38 (t, J=7 Hz, 1H), 3.23 (m, J=7 Hz, 3H), 1.94–1.63 (m, 4 H), 1.34 (d, J=7 Hz, 3H), 1.31 (m, 2H), 1.23 (m, 12 H), 0.85 (t, J=7 Hz, 3H). Elem. anal. Calcd. for C$_{25}$H$_{41}$N$_6$O$_4$+1.20 H$_2$O: C, 58.73; H, 8.56. Found: C, 58.89; H, 8.35.

EXAMPLE 4
N-[1(R)-carboxyethyl]-α-(S)-(9-aminononyl)]glycine-(L)-Arginine, N-phenylamide (9d)

MS: m/z 520 (M+); $^1$H NMR: (CD$_3$OD, δ, 400 MHz) 7.56 (d, J=7 Hz, 2H), 7.28 (dd, J=8 Hz, 2H), 7.09 (dd, J=8 Hz, 1H), 4.50 (dd, J=5 Hz, 1H), 3.17 (t, J=7 Hz, 1H), 3.22 (q, J=7 Hz, 3H), 3.12 (t, J=7 Hz, 1H), 2.72 (t, J=8 Hz, 2H), 1.96–1.64 (m, 4H), 1.51 (m, 2H), 1.39–1.26 (m, 17H). Elem. anal. Calcd. for C$_{26}$H$_{45}$N$_7$O$_4$+1.55 H$_2$O: C, 57.03; N, 17.90. Found: C, 57.20; N, 17.38.

EXAMPLE 5
N-[1(R)-carboxyethyl]-α-(S)-(n-decyl)]glycine-(L)-Leucine, N-phenylamide (9e)

MS: m/z 476 (M+); $^1$H NMR: (CD$_3$OD, δ, 400 MHz) 7.55 (d, J=7 Hz, 2H), 7.29 (dd, J=8 Hz, 2H), 7.09 (dd, J=8 Hz, 1H), 4.64 (dd, J=6 Hz, 1H), 3.92 (t, J=7 Hz, 1H), 3.62 (q, J=7 Hz, 3H), 1.86 (dt, J=8 Hz, 2H), 1.72 (dd, 2H), 1.49 (d, J=7 Hz, 3H), 1.36 (m, 1H), 1.22 ppm (m, 16H), 1.00 (dd, J=7 Hz, 6H), 0.88 (t, J=7 Hz, 3H ).

Elem. anal. Calcd. for C$_{27}$H$_{45}$N$_3$O$_4$+0.80 H$_2$O: C, 66.17; H, 9.58; N, 8.57. Found: C, 66.21; H, 8.96; N, 8.53.

---

What is claimed is:

1. A compound of formula I.

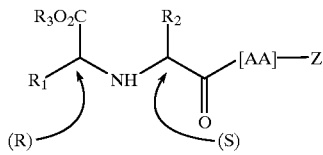

or a pharmaceutically acceptable salt thereof wherein:

$R_1$ is substituted $C_{1-6}$alkyl, wherein the substituent is selected from the group consisting of:
(a) hydrogen,
(b) carboxy,
(c)

(d) aryl wherein the aryl group is selected from the group consisting of:
(1) phenyl,
(2) naphthyl,
(3) pyridyl,
(4) furyl,
(5) pyrryl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl,
(23) isoxazolyl,
(24) thiazolyl,
(25) oxazolyl,
(26) benzthiazolyl, and
(27) benzoxazolyl, and mono and di-substituted aryl as defined above in items (1) to (27) wherein the substituents are independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, and $C_{1-6}$alkylcarbonyl;

(e)

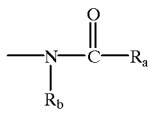

wherein $R_a$ and $R_b$ are each independently hydrogen; aryl and mono and di-substituted aryl as defined above (d); or substituted $C_{1-6}$alkyl wherein the substituent is selected from hydroxy, halo, and phenyl, or wherein $R_a$ and $R_b$ are joined such that together with the nitrogen and carbon atoms to which they are attached, there is formed a lactam or benzolactam ring wherein the lactam portion thereof is a ring of up to 8 atoms, said lactam or benzolactam have a single hetero atom;

(f)

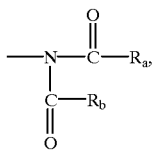

wherein $R_a$ and $R_b$ are each independently hydrogen; $C_{6-10}$aryl and mono and di-substituted aryl as defined above (d); or substituted $C_{1-6}$alkyl wherein the substituent is selected from hydroxy, halo, and phenyl, or wherein $R_a$ and $R_b$ are joined such that together with the nitrogen and carbon atoms to which they are attached, there is formed a cyclic imide wherein the imide portion thereof is a ring of up to 8 atoms, said cyclic imide has a single hetero atom;
- (g) amino and substituted amino wherein the substituent is selected from $C_{1-6}$alkyl and aryl wherein aryl is defined in (d);

$R_2$ is substituted $C_{7-12}$alkyl wherein the substituent is hydrogen, amino, $C_{1-3}$alkylamino, $C_{1-3}$dialkylamino, or hydroxyl;

$R_3$ is
- (a) H,
- (b) $C_{1-10}$alkyl,
- (c) C aryl or C aryl $C_{1-3}$alkyl, wherein the aryl group is selected from the group consisting of
  - (1) phenyl, and
  - (2) substituted phenyl, wherein the substituent is carboxy, carboxy$C_{1-3}$alkyl, aminocarbonyl, $C_{1-6}$alkylaminocarbonyl;

AA is an amino acid of formula

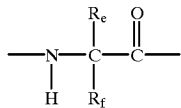

wherein $R_e$ and $R_f$ are individually selected from:
- (a) hydrogen,
- (b) $C_{1-6}$alkyl,
- (c) mercapto $C_{1-6}$alkyl,
- (d) hydroxy $C_{1-6}$alkyl,
- (e) carboxy $C_{1-6}$alkyl,
- (f) amino substituted $C_{1-6}$alkyl,
- (g) aminocarbonyl $C_{1-6}$alkyl,
- (h) mono- or di-$C_{1-6}$alkyl amino $C_{1-6}$alkyl,
- (i) guanidino $C_{1-6}$alkyl,
- (j) substituted phenyl $C_{1-6}$alkyl, wherein the substituent is hydrogen, hydroxy, carboxy, $C_{1-4}$ alkyl, or $C_{1-4}$alkyloxy,
- (k) substituted indolyl $C_{1-6}$alkyl, wherein the substituent is hydrogen, hydroxy, carboxy, $C_{1-4}$ alkyl, or $C_{1-4}$alkyloxy,
- (l) substituted imidazolyl $C_{2-6}$alkyl wherein the substituent is hydrogen, hydroxy, carboxy, $C_{1-4}$ alkyl, or $C_{1-4}$alkyloxy,
- (m) substituted pyridyl $C_{1-6}$alkyl wherein the substituent is hydrogen, hydroxy, carboxy, $C_{1-4}$ alkyl, or $C_{1-4}$alkyloxy,
- (n) substituted pyridylamino $C_{1-6}$alkyl wherein the substituent is hydrogen, hydroxy, carboxy, $C_{1-4}$ alkyl, or $C_{1-4}$alkyloxy, Z is

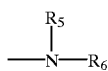

wherein $R_5$ and $R_6$ are each individually selected from the group consisting of:
- (a) H,
- (b) $C_{1-10}$alkyl,
- (c) aryl or aryl$C_{1-6}$alkyl, wherein the aryl group is selected from the group consisting of
  - (1) phenyl,
  - (2) naphthyl,
  - (3) pyridyl,
  - (4) pyrryl,
  - (5) furyl,
  - (6) thienyl,
  - (7) isothiazolyl,
  - (8) imidazolyl,
  - (9) benzimidazolyl,
  - (10) tetrazolyl,
  - (11) pyrazinyl,
  - (12) pyrimidyl,
  - (13) quinolyl,
  - (14) isoquinolyl,
  - (15) benzofuryl,
  - (16) isobenzofuryl,
  - (17) benzothienyl,
  - (18) pyrazolyl,
  - (19) indolyl,
  - (20) isoindolyl,
  - (21) purinyl,
  - (22) carbazolyl,
  - (23) isoxazolyl,
  - (24) benzthiazolyl,
  - (25) benzoxazolyl,
  - (26) thiazolyl, and
  - (27) oxazolyl.

2. A compound according to claim 1 wherein $R_1$ is substituted $C_{1-6}$alkyl, wherein the substituent is selected from the group consisting of:
- (a) hydrogen,
- (b) carboxy,
- (c)

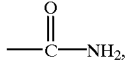

- (d) aryl or aryl $C_{1-6}$alkyl wherein the aryl group is selected from the group consisting of:
  - (1) phenyl,
  - (2) naphthyl,
  - (3) thienyl,
  - (4) imidazolyl,
  - (5) benzimidazolyl,
  - (6) pyrimidyl,
  - (7) benzofuryl,
  - (8) benzothienyl,
  - (9) indolyl, and mono and di-substituted aryl as defined above in items (1) to (9) wherein the substituents are independently selected from $C_{1-6}$alkyl, $C_{1-6}$ alkyloxy, halo, hydroxy, amino, $C_{1-6}$alkylamino, and $C_{1-6}$alkylcarbonyl;

- (e)

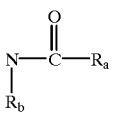

wherein $R_a$ and $R_b$ are each independently hydrogen, aryl wherein the aryl group is selected from the group consisting of:
- (1) phenyl,
- (2) naphthyl,
- (3) thienyl,
- (4) imidazolyl,
- (5) benzimidazolyl,
- (6) pyrimidyl, (7) benzofuryl,
(8) benzothienyl,
(9) indolyl,
and mono and di-substituted aryl as defined above; or substituted $C_{1-6}$alkyl wherein the substituent is selected from hydroxy, halo, and benzyl, or wherein $R_a$ and $R_b$ are joined together to form a lactam or benzolactam ring as defined above.

3. A compound according to claim 2 wherein $R_2$ is n-$C_{8-10}$alkyl and substituted n-$C_{8-10}$alkyl wherein the substituent is hydrogen or amino.

4. A compound according to claim 3 wherein $R_3$ is
   (a) H,
   (b) $C_{1-10}$alkyl,
   (c) phenyl, substituted phenyl, wherein the substituent is carboxy, carboxy $C_{1-3}$alkyl, amino carbonyl.

5. A compound according to claim 4 wherein AA is an amino acid selected from glycine, alanine, valine, leucine, isoleucine, serine, threonine, aspartic acid, asparagine, glutamic acid, glutamine, lysine, hydroxy-lysine, homohistidine, arginine, phenylalanine, tyrosine, tryptophan, cysteine, methionine, ornithine, homoserine, and citrulline.

6. A compound according to claim 4 wherein AA is

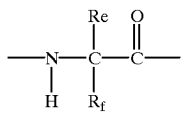

wherein $R_e$ and $R_f$ are independently selected from:
   (a) hydrogen;
   (b) $C_{1-4}$alkyl;
   (c) mercapto $C_{1-3}$alkyl;
   (d) hydroxy $C_{1-4}$alkyl;
   (e) carboxy $C_{1-4}$alkyl;
   (f) amino $C_{2-4}$alkyl;
   (g) aminocarbonyl $C_{1-4}$alkyl;
   (h) mono- or di-$C_{1-6}$alkyl amino $C_{2-4}$alkyl;
   (i) guanidino $C_{2-4}$alkyl;
   (j) substituted phenyl$C_{1-4}$alkyl, wherein the substituent is hydrogen, hydroxy, carboxy, or $C_{1-3}$ alkyl;
   (k) substituted indolyl$C_{1-4}$alkyl, wherein the substituent is hydrogen, hydroxy, carboxy, or $C_{1-3}$ alkyl;
   (l) substituted imidazolyl $C_{2-6}$alkyl wherein the substituent is hydrogen, hydroxy, carboxy, or $C_{1-4}$ alkyl;
   (m) substituted pyridyl $C_{1-6}$alkyl wherein the substituent is hydrogen, hydroxy, carboxy, $C_{1-4}$ alkyl, or $C_{1-4}$alkyloxy; and
   (n) substituted pyridylamino $C_{2-6}$alkyl wherein the substituent is hydrogen, hydroxy, carboxy, $C_{1-4}$ alkyl, or $C_{1-4}$alkyloxy.

7. A compound according to claim 6 wherein Z is

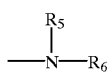

wherein $R_5$ and $R_6$ are each individually selected from the group consisting of:
   (a) H,
   (b) $C_{1-10}$alkyl, or (c) aryl, or aryl$C_{1-6}$alkyl wherein the aryl group is selected from the group consisting of:

(1) phenyl,
(2) naphthyl,
(3) thienyl,
(4) imidazolyl,
(5) benzimidazolyl,
(6) pyrimidyl,
(7) benzofuryl,
(8) benzothienyl,
(9) indolyl, and
(10) pyridyl.

8. A compound of formula I according to claim 7 which is selected from the group consisting of
   (a) N-[1(R)-carboxyethyl]-α-(S)-(9-amino-n-nonyl)]glycine-(L)-Leucine, N-phenylamide;
   (b) N-[1(R)-carboxyethyl]-α-(S)-(n-octyl)]-glycine-(L)-Leucine, N-phenylamide;
   (c) N-[1(R)-carboxyethyl]-α-(S)-(n-octyl)]-glycine-(L)-Arginine, N-phenylamide;
   (d) N-[1(R)-carboxyethyl]-α-(S )-(9-amino-n-nonyl)]glycine-(L)-Arginine, N-phenylamide;
   (e) N-[1(R)-carboxyethyl]-α-(S)-(n-decyl)]-glycine-(L)-Leucine, N-phenylamide.

9. A pharmaceutical composition for treating a matrix metalloendoproteinase-mediated disease comprising a pharmaceutical carrier and a non-toxic effective amount of the compound of claim 1.

10. A pharmaceutical composition for treating a matrix metalloendoproteinase-mediated disease comprising a pharmaceutical carrier and a non-toxic effective amount of the compound claim 1.

11. A method for inhibiting the lytic activity of metalloendoproteinases comprising administering to a subject suffering from matrix metalloendoproteinase mediated disease, an inhibitory amount of the compound of claim 1.

12. A method according to claim 11 in which the metalloendoproteinase is stromelysin.

13. A method according to claim 11 in which the metalloendoproteinase is collagenase.

14. A method according to claim 11 in which the metalloendoproteinase is gelatinase.

15. A method for inhibiting the activity of stromelysin comprising administering to a subject suffering from a stromelysin mediated disease, a therapeutic amount of the compound of claim 1.

16. A method according to claim 15 wherein the stromelysin inhibitor is administered in an amount of from about 0.01 to 50 mg of the compound per kilogram body weight.

17. A method of treating matrix metalloendoproteinase-mediated disease comprising the administration to a subject in need of such a therapeutically effective amount of a compound claim 1.

18. A method of treating matrix metalloendoproteinase-mediated disease comprising the administration to a subject in need of such a therapeutically effective amount of a compound claim 1.

19. A pharmaceutical composition for treating arthritis comprising a pharmaceutical carrier and a non-toxic effective amount of the compound of claim 1.

20. A pharmaceutical composition for treating arthritis comprising a pharmaceutical carrier and a non-toxic effective amount of the compound claim 1.

21. A method for inhibiting the lytic activity of stromelysin comprising administering to a subject suffering from stromelysin mediated arthritis, and an inhibitory amount of the compound of claim 1.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:1:

```
Arg Pro Lys Pro Leu Ala Phe Trp
1               5
```

(2) INFORMATION FOR SEQ ID NO:2:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:2:

```
Xaa Pro Leu Gly Leu Trp Ala Arg
1               5
```